United States Patent
Whitehurst et al.

(10) Patent No.: US 6,522,928 B2
(45) Date of Patent: Feb. 18, 2003

(54) PHYSIOLOGICALLY BASED ADJUSTMENT OF STIMULATION PARAMETERS TO AN IMPLANTABLE ELECTRONIC STIMULATOR TO REDUCE DATA TRANSMISSION RATE

(75) Inventors: Todd K. Whitehurst, Sherman Oaks, CA (US); Kelly H. McClure, Simi Valley, CA (US)

(73) Assignee: Advanced Bionics Corporation, Sylmor, CA (US)

( * ) Notice: Subject to any disclaimer, the term of this patent is extended or adjusted under 35 U.S.C. 154(b) by 110 days.

(21) Appl. No.: 09/812,151

(22) Filed: Mar. 19, 2001

(65) Prior Publication Data

US 2001/0037132 A1 Nov. 1, 2001

Related U.S. Application Data

(60) Provisional application No. 60/200,181, filed on Apr. 27, 2000.

(51) Int. Cl.$^7$ .............................. A61N 1/32; A61N 1/18
(52) U.S. Cl. ............................. 607/48; 607/60; 607/49; 128/903
(58) Field of Search ................................ 607/2, 48, 44, 607/60; 128/903

(56) References Cited

U.S. PATENT DOCUMENTS

| | | | |
|---|---|---|---|
| 4,524,774 A | 6/1985 | Hildebrandt | 128/421 |
| 5,097,833 A | 3/1992 | Campos | 128/421 |
| 5,324,316 A | 6/1994 | Schulman et al. | 607/61 |
| 5,748,845 A | 5/1998 | Labun et al. | 395/20 |
| 5,836,995 A | 11/1998 | McGraw et al. | 607/48 |
| 6,044,301 A * | 3/2000 | Hartlaub et al. | 607/31 |
| RE36,690 E | 5/2000 | McGraw et al. | 607/48 |
| 6,208,894 B1 * | 3/2001 | Schulman et al. | 607/2 |
| 6,424,867 B1 * | 7/2002 | Snell et al. | 607/31 |

* cited by examiner

Primary Examiner—Carl Layno
(74) Attorney, Agent, or Firm—Kenneth L. Green; Bryant R. Gold

(57) ABSTRACT

A Functional Electro Stimulation (FES) system provides physiologically based adjustment of stimulation parameters to achieve a high update rate for nerve and muscle stimulation at a reduced data transmission rate. FES systems generate electrical signals to stimulate nerves and muscles to provide movement for paraplegics and quadriplegics. Known FES systems comprise a multiplicity of microstimulators that are controlled by a single master controller. Control signals are transmitted over an RF link. A complete set of stimulation parameters comprising pulse amplitude, pulse width, and pulse frequency is initially transmitted to set initial stimulation parameters. Subsequent functional control of muscles is achieved by transmitting an increment to a single stimulation parameter. In a preferred embodiment the physiological behavior of the human body is copied by incrementing the pulse rate.

20 Claims, 3 Drawing Sheets

PHYSIOLOGICALLY BASED ADJUSTMENT OF STIMULATION PARAMETERS TO AN IMPLANTABLE ELECTRONIC STIMULATOR TO REDUCE DATA TRANSMISSION RATE

The present application claims the benefit of U.S. Provisional plication Ser. No. 60/200,181, filed Apr. 27, 2000, which application is incorporated herein by reference.

BACKGROUND OF THE INVENTION

The present invention relates to Functional Electro Stimulation FES) systems and more particularly to an improvement to known methods for providing control signals to an FES system. Such control signals are required at a high update rate to provide effective stable control of a patient's movement. The improvement provided by the present invention allows for a high effective update rate while reducing the overall data transmission rate.

Paraplegics and quadriplegics often have muscles capable of functioning, but are paralyzed due to damage to nerves that carry impulses to the muscles. Functional Electro Stimulation provides paraplegics and quadriplegics with use of their muscles by providing artificial stimulation pulses to the patient's muscles, which stimulation results in a desired movement.

Prosthetic devices have been used for some time to provide electrical stimulation to excite muscle, nerve or other cells. Some of these devices have been large bulky systems providing electrical pulses through conductors extending through the skin. Disadvantageously, complications, including the possibility of infection, arise in the use of stimulators which have conductors extending through the skin.

Other smaller stimulators are implanted which are controlled through high-frequency, modulated RF, telemetry signals. An FES system using telemetry signals is set forth in U.S. Pat. No. 4,524,774, issued Jun. 25, 1985 for "Apparatus and Method for the Stimulation of a Human Muscle." The '774 patent teaches a source of electrical energy, modulated by desired control information, to selectively control and drive numerous, small stimulators disposed at various locations within the body. Thus, for example, a desired, progressive muscular stimulation may be achieved through the successive or simultaneous stimulation of numerous stimulators, directed by a single source of information and energy outside the body.

Many difficulties arise in designing RF powered implanted stimulators which are small in size, and in passing sufficient energy and control information to the stimulators to satisfactorily operate them without direct connection. A design of a suitable, small stimulator, a microstimulator, which can be easily implanted, such as by expulsion through a hypodermic needle, is taught is U.S. Pat. No. 5,324,316 issued Jun. 28, 1994 for "Implantable Microstimulator." The '316 patent teaches all the elements required for successful construction and operation of a microstimulator. The microstimulator is capable of receiving and storing sufficient energy to provide the desired stimulating pulses, and also, is able to respond to received control information as to pulse duration, current amplitude and shape. Further, the stimulator of the '316 patent achieves a "charge balancing", that is, a balancing of current flow through the body tissue in both directions to prevent damage to the tissue which results from continued, preponderance of current flow in one direction. The '316 patent in incorporated herein by reference.

The microstimulator of the '316 patent requires a control signal comprising the amplitude, width, and frequency of the desired stimulation pulse. In order to achieve effective control of muscles, to move the patient's body in a desired manner, a pulse parameters update rate of approximately 100 Hz is required. Additionally, a plurality of microstimulators may be required to stimulate difference nerves or muscles in a coordinated manner to achieve the desired motion. The requirements for both transmission of the signals by a master control, and receipt of the signals by a multiplicity of microstimulators results in increased power consumption and potentially high error rates. What is therefore needed is a method for reducing the data rate of data that must be transmitted to achieve effective functional control of the patient's muscles.

SUMMARY OF THE INVENTION

The present invention addresses the above and other needs by providing a Functional Electro Stimulation (FES) system utilizing an initial control message, which initial control message provides a complete set of stimulation parameters for a microstimulator, followed by a sequence of high data rate control messages, which high update rate control messages provide a single stimulation parameter for the microstimulator. As a result, effective stimulation is achieved at a much lower data transmission rate than when a complete set of stimulation parameters is transmitted at the high update rate.

In the natural use of human muscles, physiological stimulation is achieved by a change of frequency of the pulse sent to a muscle. In FES systems, stimulation levels may be controlled by changing pulse magnitude, pulse width, or pulse frequency. In a preferred embodiment, the pulse magnitude, pulse width, and pulse frequency are initially set to neutral values, which neutral values may subsequently be adjusted when needed, but changes to the level of stimulation to obtain muscle contraction is achieved by controlling pulse frequency only.

In accordance with one aspect of the invention, the control of pulse frequency is achieved by sending frequency change commands at a 100 Hz transmission rate. A typical range of pulse frequencies is from 10 to 200 Hz. The preferred step size of frequency changes is ±8 Hz or ±16 Hz. If a frequency change larger than the step size is desired, the change may be achieved over several commands. Advantageously, limiting the size of the command to ±16 results in a short message length and thus facilitates high command transmission rates.

It is a further aspect of the invention to provide feedback of stimulation parameters from the microstimulators. The feedback is used to verify that the previous control messages have been correctly received. If an error is identified, the stimulation parameters may be re-initialized, or alternatively, the high data rate control message may be used to correct the error.

It is a feature of the invention to provide a Mode in the control message, which Mode indicates whether the message is the initial control message or the high data rate control message. Based on the value of Mode, the microstimulator either processes the message as the initial control message or as the high data rate control message.

It is an additional feature of the invention to provide an ID in the control message, which ID indicates which of a multiplicity of microstimulators the control message is directed to. Based on the ID contained in the message, each microstimulator either processes the message or ignores the message.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
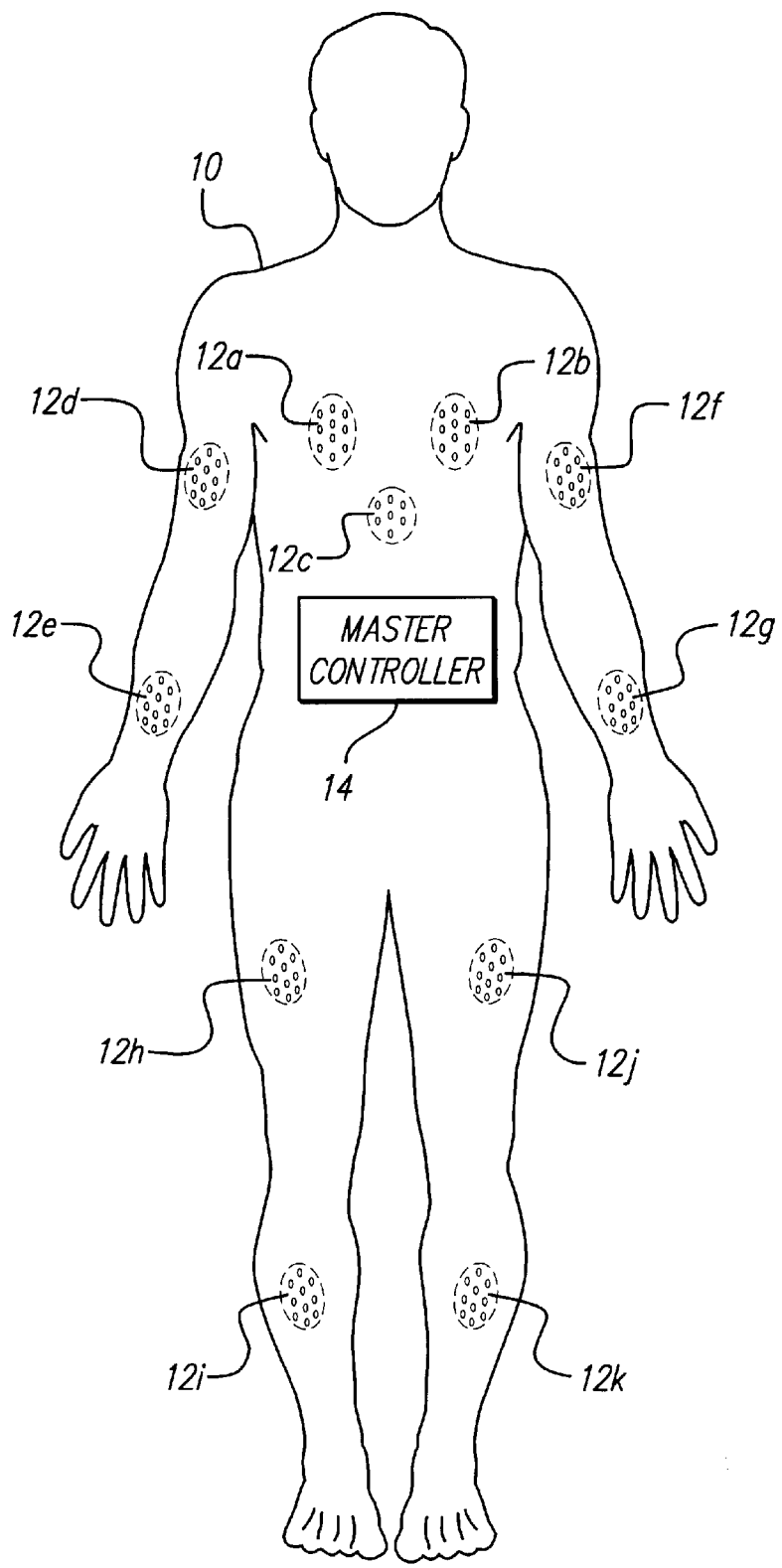
FIG. 1 depicts a master controller adjacent to a patient's leg, and a leg muscle to be stimulated.

A Functional Electro Stimulation (FES) system generates electrical signals to stimulate nerves and muscles to provide movement for paraplegics and quadriplegics. FIG. 1 shows a master controller 14 of an FES system located proximal to a patent 10. The master controller 14 transmits control signals to a multiplicity of stimulators implanted in the various muscle groups including lungs 12a, 12b, heart 12C, arms 12d–12g, and legs 12h–12k.

Figure 2:
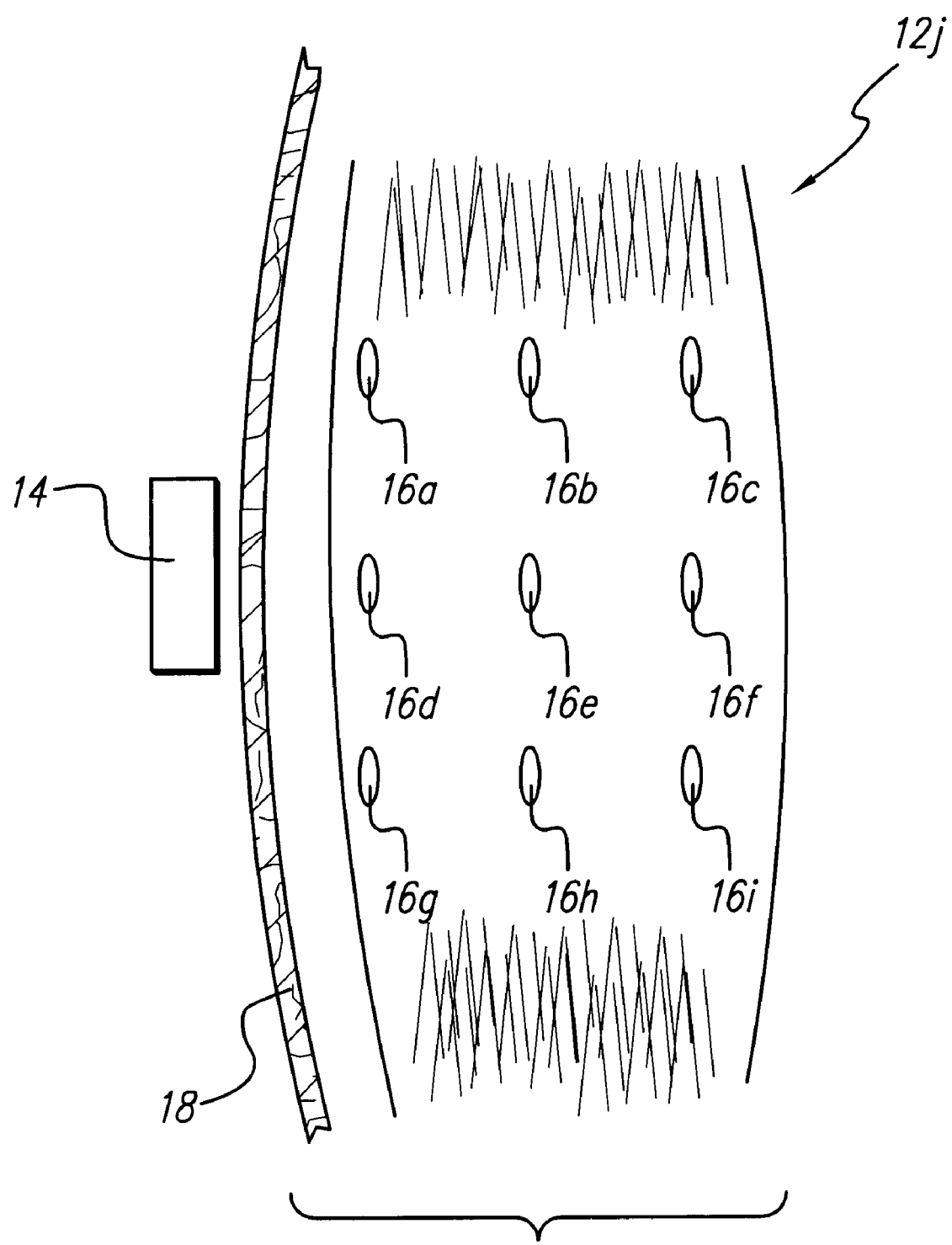
FIG. 2 shows a multiplicity of miscrostimulators within the leg muscle separated from a master controller by the patient's skin.

A view of microstimulators 16a–16i implanted in the leg muscle 12j is shown in FIG. 2. The master controller 14 is separated from the microstimulators 16a–16i by the patient's skin 18. U.S. Pat. No. 5,324,316 issued Jun. 28, 1994 for "Implantable Microstimulator" teaches the elements required for successful construction and operation of a microstimulator. Such microstimulator advantageously may be implanted through a large gauge needle and provides a minimally invasive implant procedure. However, the small size of the microstimulators dictates requirements that both the antenna for receiving the command signals, and the internal circuits for processing command signals, be as small and as low power as possible. Such size and power limitations conflict with functional requirements for high update rates for stimulation parameters to obtain stable and effective artificial control of muscles.

Figure 3:
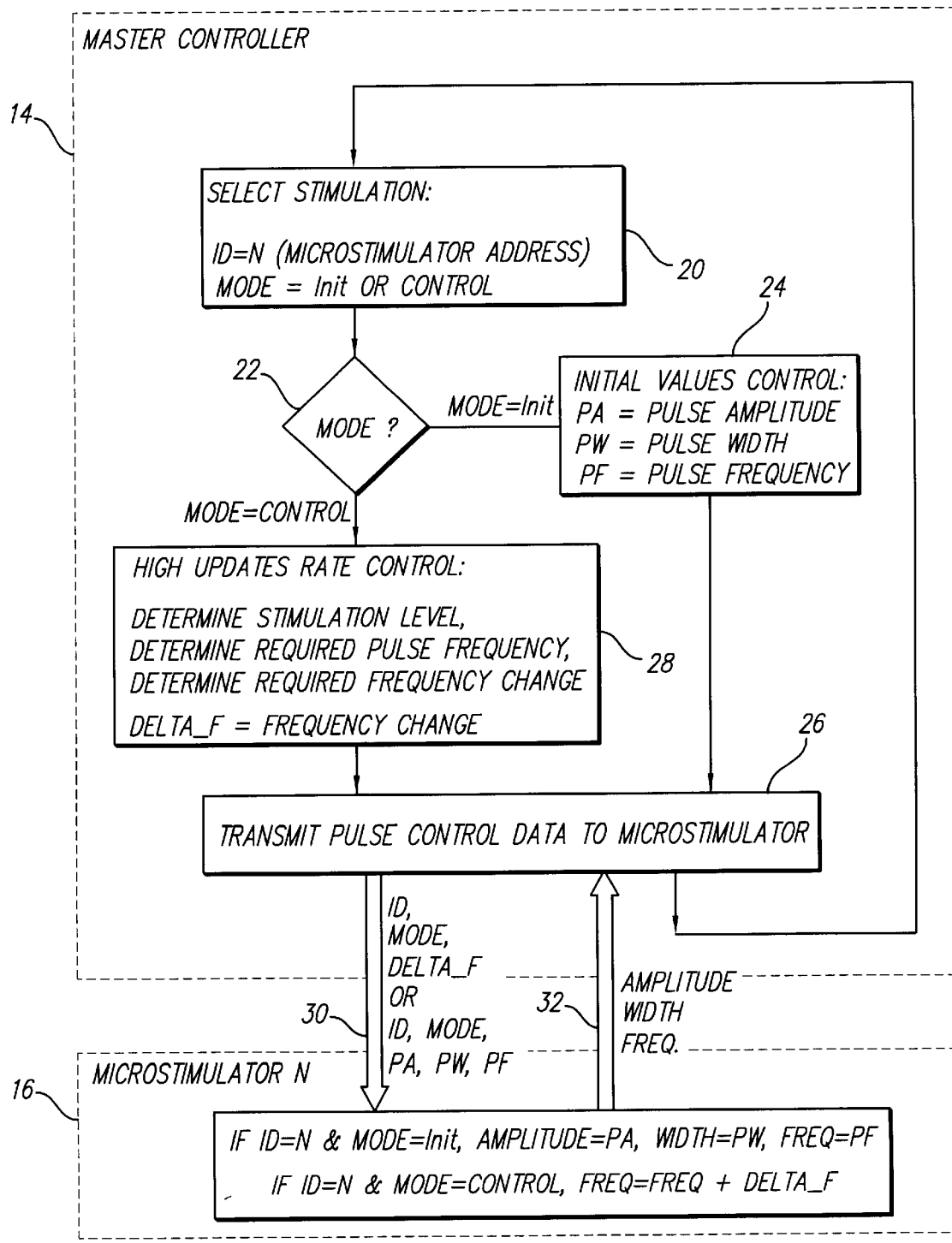
FIG. 3 depicts a functional flow diagram for a microstimulator controlled in accordance with the present invention.

FIG. 3 shows a functional diagram of a preferred embodiment of the FES system of the present invention. To accommodate both small size and high update rates, the FES system of the present invention provides an initial values control message which sets stimulation parameters to initial values, and the FES system subsequently provides a high update rate control message to update a single stimulation parameter, to efficiently control the movement of the muscles. The human body physiologically controls a muscle by changing the frequency of the pulses carried by the nerve fibers to the muscle. A preferred embodiment of the present invention similarly uses nominal values of pulse amplitude and width, which values remain constant, while the pulse frequency is adjusted to control the stimulation level.

Select stimulation 20 of the master controller 14 determines which microstimulator to control and the type of command to be provided. ID is set to the address of the selected microstimulator, and either initial values control 24 or high update rate control 28 is selected. The initial values control message is required when the FES system is turned on, and may subsequently be issued to reinitialize the microstimulator if required. A high update rate control message is required when the muscle tissue that the selected microstimulator is implanted in, is required to contract to achieve a desired body movement. The Mode is set to Init when the initial values control message is required, and Mode is set to Control when the high update rate control message is required.

Decision box 22 selects the appropriate processing based on the Mode set in the select stimulation 20. If the Mode is Init, the decision box 22 selects initial values control 24. The initial values control 24 processing sets PA to a predetermined initial pulse amplitude, PW to a predetermined pulse width, and PF to a predetermined pulse frequency. The ID, Mode, PA, PW, and PF form the initial values control message.

If Mode is Control, the decision box 22 selects high update rate control 28. The high update rate control 28 determines a desired stimulation level. A new pulse frequency required for the desired stimulation level is determined. A Delta_F command is computed by subtracting the present pulse frequency from the new pulse frequency. In a preferred embodiment the step size of changes to pulse frequency are limited to ±8 or to ±16 to keep the message size small. If a change in frequency greater than the limit is desired, the change is made over two or more transmissions. The ID, Mode, and Delta_F form the high data rate control message.

A transmit function 26 transmits messages 30 from the master controller 14 to the microstimulators 16a–16j. The microstimulator with an address corresponding to ID (in FIG. 3, microstimulator N) executes the message 30. If Mode is Init, the microstimulator sets the stimulation Amplitude to PA, Width to PW, and Freq to PF. If the Mode is Control, the microstimulator adds Delta_F to the current value of Freq. When the FES system is actively stimulating the muscles, the high data rate control message is generated and sent at a sufficient update rate to provide smooth stable motion of the body member being moved, preferably at a 100 Hz message rate.

In order to prevent data transmission errors or processing errors from accumulating, the present values of pulse Amplitude, Width, and Freq are periodically back transmitted using back telemetry 32 from the microstimulators 16a–16i to the master controller 14. These values are then compared to the intended values in the master controller. If only the pulse frequency has drifted, the error may be corrected using the high data rate control message. If other stimulation parameters have developed errors, the microstimulator may be re-initialized by a new initial control message.

Those skilled in the art will recognize that other combinations of initial and high data rate control messages fall within the scope of the present invention. For example, the pulse width and frequency may be held constant and the pulse amplitude varied to provide functional control over the patient's muscles. Similarly, any combination of two or more of the pulse parameters may be combined. In other embodiments, the electro stimulation may be provided by signals other than electrical pulses. The present invention equally applies to any form of stimulation where initial stimulation parameters may be set, and less than the entire set subsequently controlled at a high data rate. While the embodiment described above sends high data rate commands in the form of changes to existing simulation parameters, the high data rate commands may also specify the desired parameter directly.

Additionally, while the present invention focuses on Functional Electro Stimulation (i.e., providing artificially induced use of muscles to paraplegics and quadriplegics,) the present invention also applies to stimulation used to prevent muscle atrophy in paraplegics and quadriplegics, and to systems used for general muscle development. Further, the present invention may be applied to the stimulation of heart or lung muscles, or other organ related muscles. In still other applications, the microstimulator may stimulate other body tissue, including nerve tissue. The invention applies to any application of externally controlled stimulation wherein high update rates of stimulation parameters are useful.

While the invention herein disclosed has been described by means of specific embodiments and applications thereof, numerous modifications and variations could be made thereto by those skilled in the art without departing from the scope of the invention set forth in the claims.

What is claimed is:

1. A Electro Stimulation (ES) system comprising;
a controller; and
at least one stimulator;
wherein the at least one stimulator provides stimulation to body tissue, and wherein the stimulation is specified by at least one stimulation parameter; and
wherein the controller provides an initial values control message to the at least one stimulator, wherein the initial values control message contains values for the at least one stimulation parameter, and wherein the values contained in the initial values control message are a sufficient set of values to initialize the at least one stimulator; and
wherein the controller further provides a multiplicity of high update rate control message to the at least one stimulator, wherein the multiplicity of high update rate control messages update at least one parameter of the at least one stimulation parameter.

2. The ES system of claim 1 wherein the stimulation comprises electrical pulses.

3. The ES system of claim 2 wherein the electrical pulses are defined by the at least one stimulation parameter, and wherein the at least one stimulation parameter comprises: pulse amplitude, pulse width, and pulse frequency.

4. The ES system of claim 3 wherein the initial values control message comprises initial values of the pulse amplitude, the pulse width, and the pulse frequency.

5. The ES system of claim 1 wherein the controller is a master controller and the at least one stimulator is at least one microstimulator, and wherein the master controller controls the at least one microstimulator, and wherein control messages are transmitted by the master controller to the at least one microstimulator using an RF link.

6. The ES system of claim 1 wherein the at least one stimulator is at least one implantable microstimulator, wherein the at least one implantable microstimulator is implanted adjacent to the body tissue which the at least one implantable microstimulator stimulates.

7. The ES system of claim 6 wherein the body tissue comprises nerve tissue and muscle tissue.

8. The ES system of claim 6 wherein the at least one implantable microstimulator is implantable through a large gauge needle.

9. The FES system of claim 1 wherein the initial values control message includes a Mode, wherein the Mode specifies that a message is the initial values control message, and wherein the initial values control message further includes an ID, wherein the ID specifies which of the at least one stimulators the initial values control message is directed to; and wherein the high update rate control message includes a Mode, where in the Mode specifies that the message is a high update rate control message, and wherein the high update rate control message further includes an ID, wherein the ID specifies which of the at least one stimulator the high update rate control message is directed to.

10. The FES system of claim 1 wherein the multiplicity of high update rate control messages update the pulse frequency.

11. The FES system of claim 1 wherein the multiplicity of high update rate control messages are transmitted to the at least one stimulator at about a 100 Hz data rate.

12. The ES system of claim 1 wherein the ES system comprises a Functional Electro Stimulation (FES) system.

13. A method for providing a high update rate for Functional Electro Stimulation (FES) of body tissue comprising the steps of;

implanting a microstimulator;

placing a master controller near the location of the microstimulator;

transmitting an initial values control message from the master controller to the microstimulator, wherein the initial values control message includes init data sufficient to initialize a stimulation parameter set of the microstimulator;

initializing the stimulation parameter set based on the initial values control message;

transmitting a multiplicity of high update rate control messages from the master controller to the microstimulator, wherein each one of said high update rate control messages contains update data to update a member of the stimulation parameter set;

receiving the high update rate control message in the microstimulator;

updating the stimulation parameter set based on the update data in the high update rate control messages;

stimulating the body tissue in accordance with the stimulation parameter set.

14. The method of claim 13 wherein the initial values control message includes a Mode and an ID, and the microstimulator include an address, and wherein the step of initializing the stimulation parameter set comprises initializing the stimulation parameter set when both the Mode in the initial values control message specifies that the message is the initial values control message, and the ID in the initial values control message matches the address of the microstimulator; and wherein the multiplicity of high update rate control messages includes the Mode and the ID, and wherein the step of updating the stimulation parameter set, comprises updating the stimulation parameter set when both the Mode in the present one of the multiplicity of high update rate control messages specifies that the message is one of the multiplicity of high update rate control messages, and the ID in the present one of the multiplicity of high update rate control messages matches the address of the microstimulator.

15. The method of claim 13 wherein the step of stimulating the body tissue comprised stimulating the body tissue with electrical pulses, wherein the stimulation parameter set comprises pulse amplitude, pulse width, and pulse frequency.

16. The method of claim 13 wherein the body tissue comprises nerve issue and muscle tissue.

17. The method of claim 13 wherein the step of transmitting the initial values control message, comprises transmitting the initial values control message from the master controller to the microstimulator using an RF link; and
   wherein the step of transmitting the multiplicity of high update rate control messages comprises transmitting the multiplicity of high update rate control messages from the master controller to the microstimulator using an RF link.

18. The method of claim 13 wherein the step of updating the stimulation parameter set comprises adding the update data to a corresponding element of the stimulation parameter set.

19. The method of claim 13 wherein the stimulation parameter set included pules frequency, and wherein the step of updating the stimulation parameter set comprises adding the update data to the pulse frequency.

20. The method of claim 19 wherein the step of transmitting a multiplicity of high update rate control messages includes transmitting a multiplicity of high update rate control messages at about a 100 Hz data rate.

* * * * *